(12) United States Patent
Lu

(10) Patent No.: US 6,733,801 B2
(45) Date of Patent: *May 11, 2004

(54) METHOD OF USING FERMENTED GLYCINE MAX (L) EXTRACT FOR ENHANCING NATURAL KILLER CELL ACTIVITY

(75) Inventor: Kung-Ming Lu, Taipei (TW)

(73) Assignee: Microbio Co., Ltd., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 10/178,364

(22) Filed: Jun. 25, 2002

(65) Prior Publication Data

US 2003/0003169 A1 Jan. 2, 2003

Related U.S. Application Data

(63) Continuation-in-part of application No. 09/812,579, filed on Mar. 21, 2001, now abandoned.

(51) Int. Cl.$^7$ .......................... A61K 35/78; A61K 35/00
(52) U.S. Cl. ...................................... 424/759; 424/115
(58) Field of Search ............................... 424/757, 115; 514/885

(56) References Cited

U.S. PATENT DOCUMENTS 5,891,492 A * 4/1999 Ishigaki
6,303,161 B1 * 10/2001 Takebe et al.

FOREIGN PATENT DOCUMENTS

| JP | 10210947 | * | 8/1998 |
| JP | 10229841 | * | 9/1998 |
| JP | 11018759 | * | 1/1999 |
| JP | 2000004868 | * | 1/2000 |

OTHER PUBLICATIONS

Duke et al. 2002. Handbook of Medicinal Herbs. CRC Press, pp. 686–687.*
Webster's II New Riverside University Dicitonary. 1988. Definition of "soybean" on p. 1112.*

* cited by examiner

Primary Examiner—Christopher R. Tate
(74) Attorney, Agent, or Firm—Rosenberg, Klein & Lee

(57) ABSTRACT

This invention relates to a use of a fermented *Glycine max* (L.) extract prepared by fermenting an aqueous *Glycine max* (L.) extract with at least one lactic acid bacteria together with at least one yeast, in enhancing Natural Killer (NK) cell activity. In particular, the fermented *Glycine max* (L.) extract can be used in preventing and/or treating a disease in which NK cell activation is implicated in a subject, such as cancer, infectious diseases and modulating the immune system.

6 Claims, No Drawings

METHOD OF USING FERMENTED GLYCINE MAX (L) EXTRACT FOR ENHANCING NATURAL KILLER CELL ACTIVITY

CROSS-REFERENCE TO RELATED APPLICATION

This is a continuation-in-part of patent application Ser. No. 09/812,579, filed Mar. 21, 2001 now abandoned.

BACKGROUND OF THE INVENTION

1. Field of the Invention

This invention relates to the use of a fermented *Glycine max* (L.) extract in enhancing natural killer cell (NK cell) activity, preventing and/or treating a disease in which natural killer cell (NK cell) activation is implicated in a subject, such as cancer and infectious diseases. The present invention also relates to the use of increasing immunity in a subject, such as chemotherapy and radiotherapy.

2. Description of the Prior Art

Natural killer (NK) cells are a subset of lymphocytes active in the immune system and representing an average 15% of mononuclear cells in human peripheral blood. NK cells have been found to play a primary role in preventing and removing cancer cells in the body and removing many types of viruses. Their specific function is to kill infected and cancerous cells. Many researches reported that the NK cell activity is associated with cancer and infectious diseases (Yamazaki et al., Oncology Reports. 2002, Vol. 9, pp. 359–363; Rosenberg et al., Cancer Research (suppl.) 1991, Vol. 51, pp. 5074–5079; Britteenden et al., 1996, Cancer, 1996, Vol. 77, No. 3, pp. 1226–1243; U.S. Pat. Nos. 5,082,833; 4,883,662). Moreover, the value of NK cell activity was further studies and confirmed for the linkage of primary tumors prevention and metastasis inhibition of existing malignancies in a series of researches. Therefore, defective or absent NK cell activity is associated with a spectrum of human diseases. According to the Center for Disease Control, low NK cell activity is present in all illness. NK cell function appears to be a biological marker for disease and is an important indicator for declining or improving health. Thus enhancement of NK cell activity has become an attractive approach for effective treatment or therapy of cancer and infections.

A substance having an efficacy in enhancing NK cell activity is useful as an agent for preventing or treating diseases. Soybeans are one concentrated source of isoflavones in human diet. They also contain many compounds including saponins, phytosterols, soybean phytates, protease inhibitors, phenolic acids, complex sugars, boron, lecithin, omega-3 fatty acids and folic acid. They can impart health benefits. Many eastern traditional foods, such as tembe and natto, are produced from the fermentation of soybeans. For example, tembe is roduced by fermenting soybean with *Rhizopus oligosporus, R. oryzae, R. arrihizus* and *R. stolonifer*. Natto is produced by fermenting soybean with *Bacillus natto*. The traditional fermented foods can be used as a superior protein origin. However, none of the prior art discloses that any known fermented soybean foods and soybeans have an efficacy in enhancing NK cell activity.

SUMMARY OF THE INVENTION

This invention relates to a use of a fermented *Glycine max* (L.) extract, which is prepared by fermenting an aqueous *Glycine max* (L.) extract with at least one lactic acid bacteria together with at least one yeast, in increasing NK cell activity.

One objective of the invention is to provide a method of enhancing NK cell activity in a subject, comprising administering an effective amount of a fermented *Glycine max* (L.) extract to the subject in need of thereof, wherein the fermented *Glycine max* (L.) extract is prepared by fermenting an aqueous *Glycine max* (L.) extract with at least one lactic acid bacteria together with at least one yeast. Particularly, *Glycine max* (L.) is soybean or black soybean. More particularly, the fermented *Glycine max* (L.) extract of the invention include the fermented soybean extract and fermented black soybean extract.

Another objective of the invention is to provide a method of preventing and/or treating a disease in which NK cell activation is implicated in a subject, comprising administering an effective amount of the fermented *Glycine max* (L.) extract to the subject in need of thereof. In particular, the fermented *Glycine max* (L.) extract of the invention can be used in preventing and/or treating a disease in which NK cell activation is implicated in a subject, such as cancer and infectious diseases.

The foregoing objective and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE INVENTION

The invention relates to a new use of a fermented *Glycine max* (L.) extract for enhancing NK cell activity and the diseases implicated in the NK cell activation, wherein the fermented *Glycine max* (L.) extract is prepared by fermenting an aqueous *Glycine max* (L.) extract with at least one lactic acid bacteria together with at least one yeast. It is unexpectedly found that the fermented *Glycine max* (L.) extract can effectively enhance NK cell activity in a low level.

In particular, the fermented *Glycine max* (L.) extract of the invention can be used in preventing and/or treating a disease in which NK cell activation is implicated in a subject, such as cancer and infectious diseases. In addition, the fermented soybean extract of the invention can also be used in modulating immune system in which NK cell activation is implicated in a subject, such as chemotherapy and radiotherapy.

Process for Producing the Fermented Soybean Extract

The fermented *Glycine max* (L.) extract is made by fermentation of an aqueous *Glycine max* (L.) extract with at least one lactic acid bacteria together with at least one yeast, followed by sterilization, e.g. by heat, of the fermented liquid with optional filtration and concentration.

According to the invention, the preferred *Glycine max* (L.) used in the preparation of the fermented *Glycine max* (L.) extract is selected from the group consisting of soybean and black soybean. More particularly, the fermented *Glycine max* (L.) extract of the invention is the fermented soybean extract or fermented black soybean extract.

The fermented *Glycine max* (L.) extract is produced by fermentation of *Glycine max* (L.) extract with at least one lactic acid bacteria, e.g. one or more strains of a Lactobacillus species or several strains of a number of Lactobacillus species, together with at least one yeast, e.g. one or more strains of a Saccharomyces species or several strains of a number of Saccharomyces species. The fermentation of the aqueous *Glycine max* (L.) extract with one or more lactic acid bacteria and the optional Saccharomyces species can be carried out sequentially in any order or simultaneously, preferably simultaneously.

If more than one microbe is used in the fermentation, the fermentation can be conducted with the microbes sequentially or simultaneously. Preferably, an aqueous extract of non-genetically modified organic *Glycine max* (L.) of selected grade is used as a starting material. Preferably, the fermentation is carried out using a heterogeneous culture of Lactobacillus, for example, a culture of 5, 10, 15, 20, 25 or 30 strains of Lactobacillus and at least one yeast is added to the heterogeneous culture of Lactobacillus. The strains of Lactobacillus that can be used include, for examples, *Lactobacillus acidophilus* CCRC 10695, 14026, 14064, 14065 and/or 14079, *Lactobacillus delbrueckii bulgaricus* CCRC 10696, 14007, 14009, 14010, 14069, 14071, 14098 and/or 16054, *Lactobacillus lactis lactis* CCRC 10791, 12267, 12306, 12312, 12315, 12323, 14016, 14015 and/or 14117, *Lactobacillus kefir* CCRC 14011, and/or *Lactobacillus kefiranofaciens* CCRC 16059. The yeast that can be used include, for example, *Saccharomyces cerevisiae* CCRC 20577, 20578, 20581, 21494, 21550, 21797, 21805, 22138, 22234, 22337, 22731 and/or 22728, and/or *Candida kefyr* CCRC 21269, 21742 and/or 22057. After fermentation, the fermented liquid is sterilized, e.g. by heat or irradiation, preferably by heat, to obtain a sterilized liquid. Preferably, the sterilized liquid is filtered or centrifuged, preferably filtered, to remove most or all of the dead microbes to obtain the fermented *Glycine max* (L.) extract. More preferably, the filtration step is followed by removal of some of the water from the filtrate to concentrate the fermented liquid to obtain the fermented *Glycine max* (L.) extract. Unless otherwise specified, the tests performed in this application involved the fermented *Glycine max* (L.) extract after the concentration step. Optionally, the fermented *Glycine max* (L.) extract can be dried, e.g. via lyophilization, to obtain the fermented *Glycine max* (L.) extract in a powder form.

The process can be carried out by mixing organic *Glycine max* (L.) (with fat removed) with distilled water at a ratio of 1:10. The mixture is heated at 100° C. for 30 minutes and then filtered to obtain a *Glycine max* (L.) extract. Beef and kelp are boiled in distilled water for 30 minutes to obtain a broth. Salt, sugar and agar are added to produce a special agar medium. The lactic acid bacteria and yeast strains are added to the special agar medium. The lactic acid bacteria with the optional inclusion of the yeast in the medium are transferred to the *Glycine max* (L.) extract and incubated at 36–43° C. for 45–50 hours. Preferably, the various strains of the microbes are grouped according to similar growth characteristics, e.g. any requirements of unique nutrient medium, whether the microbial strains could produce a good smell after fermentation and whether the grouped microbes can survive in the unique condition, so that groups of the microbes are added to the *Glycine max* (L.) extract separately before the incubation. The purpose of this step is to reduce any negative interaction among the various strains. Also preferably, equal proportion of the different groups of microbial strains are added to the *Glycine max* (L.) extract before the incubation and the resulting extract is incubated at 40° C. for 45–47 hours. Upon completion of the incubation period, the heterogeneous culture is then transferred to the *Glycine max* (L.) extract again and incubated at 36–43° C. for 100–150 hours. The final fermented extract is heat sterilized and filtered; and 95% of the water content of the filtrate is removed in a concentrator to obtain a fermented *Glycine max* (L.) extract in a concentrated or condensed form. The upper layer is then filtered through porcelain, and thereafter dispensed in containers and sealed.

Within the scope of the present invention is a fermented extract of a Chinese herb prepared in a process similar to the one described above with the substitution of the soybean with the Chinese herb. The fermented extract of the Chinese herbs can be *Glycyrrhiza uralensis* Fish, *Lycium barbarum*, *Coix lacryma-jobi* L var., ma-yune Stapf, *Sophora tonkinensis* gapnep., *Cassia btusifolia.*, *Scutellaria baicalensis* Georgi, *Artemisia capillaries* Thunb., *Coptis chinensis* Frsnch., *Gentiana scabra* Bge., *Nelumbo nucifera* Gaertn., *Chrysantheiferamum morfolium* Ramat., *Gardenia jasminoides* Ellis, *Hordeum vulgare* L., *Cinnamomum cassia* Presl, Raph, anus sativus L., *Dioscorea opposita* Thunb., *Angelica sinensis* (Oliv.), *Ligusticum chuanxiong* Hort., *Notopteygium incisum*, *Paeonia lactiflora* Pall., *Allium satium* L., *Schisandra chinensis*(Turcz.)Baill, *Rehmannia glutinosa* Libosch., *Acanthopanax gracilistylus* W. W. Smith, *Equus asinus* L., *Ligustrum lucidum* Ait., *Phaseolus radiatus* L., *Triticum aestivum* L., *Dolichos lablab* L., *Atractylodes macrocephala* Koidz., *Saposhnikovia divaricata*, *Lonicera japonica* Thund., *Cinnamomum cassia* Presl, *Zingiber officinale* Rosc., *Gastrodia elata* Bl., *Asparagus cochinchinensis*(Liur.)Merr., *Dendrobiun loddigesii* Rolfe., and *Sesamum indicum* L.

Use in Enhancing NK Cell Activity

Natural Killer cells, a small subset of peripheral blood lymphocytes, mediate a variety of functions that are important in human health and diseases. In addition to their role in control of metastasis and infections, NK cells participate in immunoregulation, haematopoiesis, reproduction and neuroendocrine interactions. NK cell activity and NK cell count are not the same. NK cells may be present in sufficient numbers, but unless they are activated they are ineffective in doing their job. Decreased NK cell activity is linked to the development and progression of many diseases, moreover to radiotherapy and chemotherapy. Therefore, NK cell function appears to be a biological marker for disease and is an important indicator for declining or improving health. In addition to that, NK cell activity serves as an important prognostic factor for a variety of cancers.

Studies in the invention have demonstrated that the fermented *Glycine max* (L.) extract can increase NK cell activity superior than known fermented soybean foods and unfermented soybean. The increase of NK cell activity by the fermented *Glycine max* (L.) extract can have cytotoxicity effects by modulating signal transduction, modulating growth factor activation and killing the cancer cells and/or infectious cells. And the increased NK cell activity can result in suppression of tumor growth.

Given the above, the fermented *Glycine max* (L.) extract of the invention has the superior effects on the enhancement of NK cell activity and thus can be used in preventing and/or treating a disease in which increasing NK cell activity is implicated in a subject, such as cancer, infectious disease and immune modulation. In an embodiment of the invention, the fermented *Glycine max* (L.) extract can be used as an anti-inflammation agent, an anti-cancer agent or an agent for promoting immune function.

Use for Anti-cancer Agent

The fermented *Glycine max* (L.) extract of the present invention has anti-cancer activity for the treatment and/or prevention of cancer, whilst overcoming one or more disadvantages of prior art chemotherapeutic agents available for the treatment cancer. The cancer that can be treated with the fermented *Glycine max* (L.) extract includes the most prevalent types of cancer in the human population, namely breast cancer, colon cancer, cervix, prostate, kidney, lung, colon and liver cancers.

In cancer cells, the fermented *Glycine max* (L.) extract of the present invention can induce one or more effects of inhibition of cell proliferation, induction of cell differentiation, induction of apoptosis (programmed cell death), and/or cell cycle blocking. As a consequence, the extract of the present invention have wide ranging activity against cancer cells and are accordingly effective in the treatment and/or prevention of cancers including benign prostatic hypertrophy, prostatic cancer, breast cancer, uterine cancer, leukemia, ovarian cancer, endometrial cancer, cervical cancer, colon cancer, testicular cancer, lymphoma, rhabdosarcoma, neuroblastoma, pancreatic cancer, lung cancer, brain tumor, skin cancer, gastric cancer, oral cancer, liver cancer, laryngeal cancer, bladder cancer, thyroid cancer, liver cancer, kidney cancer and nasoharyngeal carcinoma.

Use for Promoting Immune Function

In addition to their role in the control of cancer, NK cells helps in the regulation of other aspects of the immune system which effects our overall health. Immunotherpay to help increase NK cell activity is becoming available and will become more widely used as knowledge of the immune system increases. In vitro study indicated that the fermented *Glycine max* (L.) extract of the invention improved immune function. The effect of the fermented *Glycine max* (L.) extract on modulation of the immunity of animals (Bala/c mice) was studied by treating the animal with the fermented *Glycine max* (L.) extract combined with or without a challenge with various mitogens including lipopolysachrride, concanavalin A and phytohaemagglutilin. Spleen cell proliferation assay indicated that the fermented *Glycine max* (L.) extract could be related with T & B cell interaction in immunity modulation. The fermented *Glycine max* (L.) extract can also be correlated with anti-inflammation reaction. The *Glycine max* (L.) extract also enhanced phagocytosis activity of macrophages by 71%. Similar results were found with in vivo studies in mice. It was also demonstrated that the anti-tumor effect of fermented *Glycine max* (L.) extract is mediated by cytokines released. Conditioned medium from fermented *Glycine max* (L.) extract-stimulated peripheral blood mononuclear cells by 45–56%. Levels of interleukin-1b, interleukin-b and tumor necrosis factor-a were much higher than those of untreated control. Since untreated Macrophages and T Lymphocytes produced little or no cytokine and normal mononuclear cells did not suppress leukemic cell growth, the anti-tumor activity is speculated to be derived from elevated level of cytokine.

Administration of the Fermented *Glycine max* (L.) Extract

In this invention, the fermented *Glycine max* (L.) extract may be administered alone or in a composition comprising the fermented *Glycine max* (L.) extract and a pharmaceutically acceptable carrier, diluent and/or excipient. Preferably, the fermented *Glycine max* (L.) extract is fermented soybean extract or fermented black soybean extract. The fermented *Glycine max* (L.) extract may be administered at a dose of about 0.001 to 40 ml/kg body weight, with a maximum dose of 2000 ml per person per administration. Preferably, the dose of the fermented *Glycine max* (L.) extract is 0.01 to 20 ml/kg, more preferably 0.1 to 5 ml/kg, body weight of the subject. These doses are based on the fermented *Glycine max* (L.) extract in the concentrated form, but appropriate doses of the fermented *Glycine max* (L.) extract in the unconcentrated form or dry powder form can be calculated accordingly. The dose can be adjusted based on the health condition of the subject or the disease to be prevented or treated.

The fermented *Glycine max* (L.) extract was demonstrated to be highly safe for daily intake of 1–10 ml on a long-term basis in a 6 months chronic toxicity study of rodents. Mice receiving a dose of 10 ml/kg and 1 ml/kg for 28 days did not exhibit any significant difference or abnormal symptom in a subacute oral toxicity study. No signs of gross toxicity or mortality were observed in two groups of tested animals administered 20 ml/kg and 1 ml/kg in an acute oral toxicity study of rodents. The fermented *Glycine max* (L.) extract was demonstrated to be non-mutagenic in Ames test, to not cause chromosomal damage in mammalian cells in vitro and to not induce micronuclei in bone marrow cells in ICR mice tested.

This invention will now be described with reference to the following non-limiting examples.

After white mice (Balb/c) have been fed a fermented soy extract for three weeks, the NK (natural killer) cell activity is examined as follows: Three groups are tested. The first group of Balb/c white mice are fed with PBS buffer solution, the second group is fed with 0.1% FSE, and the third group is fed with 0.4% of FSE.

TABLE 1

| Group | NK cell activity, killing percentage |
|---|---|
| Group fed with PBS cushioning liquid | 24.8 ± 4.8 |
| 0.1% FSE | 33.2 ± 4.2** |
| 0.4% FSE | 35.1 ± 5.9** |

Each value was expressed as Mean±SD. The values were analyzed by one-way ANOVA test **, significantly different at 0.01 level compared with control.

To evaluate the effect of FSE on the restoration of chemotherapy induced NK function depression, we examined changes in NK activity before and after fermented soy extract was administered in 18 patients who underwent chemotherapy. The result shows overall NK activity was increased by orally administration of fermented soy extract from 5.751% to 13.493% (p=0.02). The NK activity percentage was shown in below Table 2:

TABLE 2

| NK ACTIVITY: Clinical evaluation (n = 18) | | |
|---|---|---|
| Treatment | NK activity (%, by K562, E/T = 25) | p Value |
| Control (C/T) | 5.751 | |
| FSE (C/T + FSE) | 13.493 | 0.02 |

The result shown above is a open-label, cross-over, no placebo control designed clinical evaluation.

While certain novel features of this invention have been shown and described and are pointed out in the annexed claim, it is not intended to be limited to the details above, since it will be understood that various omissions, modifications, substitutions and changes in the forms and details of the device illustrated can be made by those skilled in the art without departing in any way from the spirit of the present invention.

I claim:

1. A method of using enhancing natural killer cell activity in a subject a fermented *Glycine max* (L.) extract comprising the steps of:
   (a) fermenting a mixture of an aqueous *Glycine max* (L.) extract, at least one lactic acid bacteria and a yeast to form a fermented liquid;
   (b) sterilizing said fermented liquid;
   (c) filtering said fermented liquid to remove particulate matter therein to form said fermented *Glycine max* (L.) extract; and,
   (d) administering said extract in a predetermined amount to a human subject in need thereof wherein the amount is effective to enhance natural killer cell activity for treating and/or reducing a susceptibility to a disease process in which there is insufficient natural killer cell (NK cell) activation to resist and/or prevail against said disease process.

2. The method of using a fermented *Glycine max* (L.) extract as claimed in claim 1, wherein said *Glycine max* (L.) is black soybean.

3. The method of using a fermented *Glycine max* (L.) extract as claimed in claim 1, wherein said fermented *Glycine max* (L.) extract comprises fermented black soybean extract.

4. A method of using enhancing natural killer cell activity in a subject a fermented *Glycine max* (L.) extract comprising the steps of:
   (a) fermenting a mixture of an aqueous *Glycine max* (L.) extract, at least one lactic acid bacteria and a yeast to form a fermented liquid;
   (b) sterilizing said fermented liquid;
   (c) filtering said fermented liquid to remove particulate matter therein, to form said fermented *Glycine max* (L.) extract; and,
   (d) administering said extract in a predetermined amount to a human subject in need thereof wherein the amount is effective to enhance natural killer cell activity for enhancing at least one immune system function of said human subject in whom there is insufficient natural killer cell activation to resist and/or prevail against a disease process.

5. The method of using a fermented *Glycine max* (L.) extract as claimed in claim 4, wherein said *Glycine max* (L.) is black soybean.

6. The method of using a fermented *Glycine max* (L.) extract as claimed in claim 4, wherein said fermented *Glycine max* (L.) extract comprises fermented black soybean extract.

* * * * *